United States Patent [19]

Sevrin et al.

[11] Patent Number: 5,380,742
[45] Date of Patent: Jan. 10, 1995

[54] 4H-THIENO[3,4-C]PYRROLE DERIVATIVES

[75] Inventors: Mireille Sevrin, Paris; Jacques Menin, St. Germain Lembron; Christian Maloizel, Meudon, all of France; Juan A. Diaz Martin, Madrid, Spain; Ulpiano Martin Escudero Perez, Madrid, Spain; Manuel Bedoya Zurita, Madrid, Spain; Gregorio Del Sol Moreno, Madrid, Spain; Maria D. Jimenez Bargueno, Madrid, Spain; Magali Romanach Ferrer, Madrid, Spain

[73] Assignee: Synthelabo, Le Plessis Robinson, France

[21] Appl. No.: 156,780

[22] Filed: Nov. 24, 1993

[30] Foreign Application Priority Data

Nov. 24, 1992 [FR] France ............................ 92 14065
Jun. 22, 1993 [FR] France ............................ 93 07538

[51] Int. Cl.⁶ .................. A61K 31/415; C07D 403/14
[52] U.S. Cl. .................... 514/397; 548/311.7; 548/453
[58] Field of Search .............. 514/397; 548/311.7, 548/453

[56] References Cited

U.S. PATENT DOCUMENTS 5,190,938  3/1993  Badorc et al. ................... 514/215
5,276,009  1/1994  Muenster et al. ................ 504/284

FOREIGN PATENT DOCUMENTS 0238753  9/1987  European Pat. Off. .

OTHER PUBLICATIONS

D. J. Zwanenburg et al., "Steric Inhibition of Intramolecular Cyclizations by ortho Substituents, The Synthesis of 1H,3H-Thieno[3,4-c]thiophene, Its 2,2-Dioxide, and 5-Ethyl-5,6-dihydro-4H-thieno[3,4-c]pyrrole," The Journal Of Organic Chemistry, vol. 34, No. 2, pp. 333-340, Feb. 1969.

Primary Examiner—Mary C. Lee
Assistant Examiner—Jacqueline Haley
Attorney, Agent, or Firm—Wegner, Cantor, Mueller & Player

[57] ABSTRACT

Pyrrole derivatives of formula:

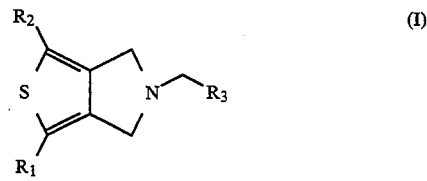

in which $R_1$ represents a hydrogen or halogen atom, a linear or branched $C_{1-6}$ alkyl group, a $C_{3-6}$ alkenyl group, a $C_{1-4}$ alkoxymethyl group, benzyl, a phenyl group optionally substituted by one or more halogen atoms or alkyl radicals, a $CO_2R$ group in which R represents a linear or branched $C_{1-4}$ alkyl radical, phenyl or benzyl, or a $CONR'R''$ group in which R' and R'' each represent, independently of one another, a hydrogen atom or a linear or branched $C_{1-4}$ alkyl radical, $R_2$ represents a hydrogen or halogen atom or a linear or branched $C_{1-4}$ alkyl group, and $R_3$ represents a 4,5-dihydro-1H-imidazol-2-yl or 1H-imidazol-4-yl group, and their addition salts with pharmaceutically acceptable acids are useful in therapeutics as $\alpha_2$-antagonists, and $\alpha_1$-agonists.

8 Claims, No Drawings

4H-THIENO[3,4-C]PYRROLE DERIVATIVES

The present invention relates to pyrrole derivatives, their preparation and their use in therapeutics.

The compounds of the invention have the general formula:

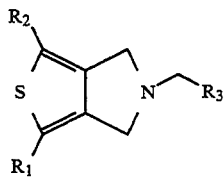

(I)

in which
- $R_1$ represents a hydrogen or halogen atom, a linear or branched $C_{1-6}$ alkyl group, a $C_{3-6}$ alkenyl group, a ($C_{1-4}$ alkoxy)methyl group, benzyl, a phenyl group unsubstituted or substituted by one or more halogen atoms or alkyl radicals, a $CO_2R$ group in which R represents a linear or branched $C_{1-4}$ alkyl radical, phenyl or benzyl, or a $CONR'R''$ group in which R' and R'' each represent, independently of one another, a hydrogen atom or a linear or branched $C_{1-4}$ alkyl radical,
- $R_2$ represents a hydrogen or halogen atom or a linear or branched $C_{1-4}$ alkyl group,
- and $R_3$ represents a 4,5-dihydro-1H-imidazol-2-yl or 1H-imidazol-4-yl group. These compounds form salts with pharmaceutically acceptable acids, which are part of the invention.

The compounds of formula (I) may be prepared according to the process represented in the following reaction Scheme 1:

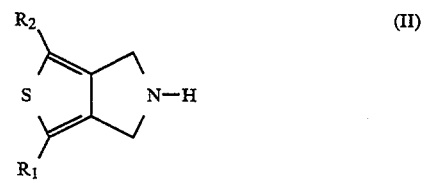

in which $R_1$ and $R_2$ have the meanings given above, with 2-chloromethyl-4,5-dihydro-1H-imidazole or 4-chloromethyl-1-triphenylmethylimidazole, preferably in a solvent such as dimethylformamide, in the presence of N,N-diisopropylethylamine, in an ultrasonic bath, to produce respectively the compound of formula (I) in which $R_3$ is the 4,5-dihydro-1H-imidazol-2-yl group or a 1-triphenylmethylimidazol-4-yl derivative of formula (Ia) which is then deprotected to give the compound of formula (I) in which $R_3$ is the 1H-imidazol-4-yl group.

The compounds of formula (I) in which $R_3$ is a 4,5-dihydro-1H-imidazol-2-yl group can also be prepared according to the process represented in Scheme 2:

Reaction Scheme 2

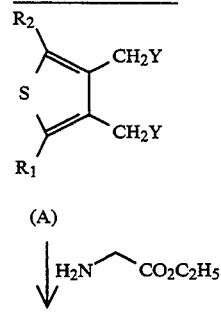

(A)

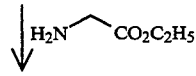

Reaction Scheme 1

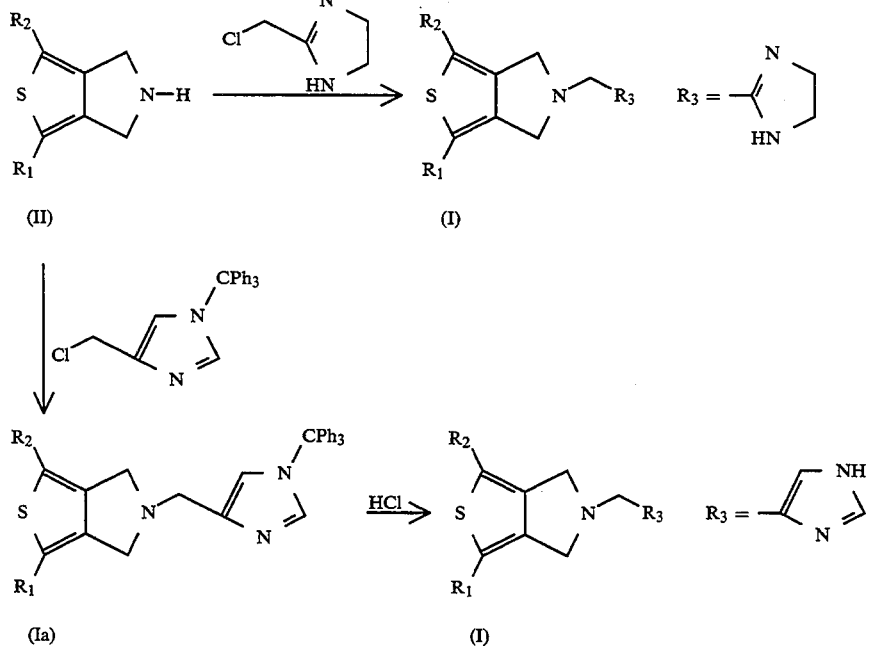

This process consists in reacting a compound of formula:

-continued
Reaction Scheme 2

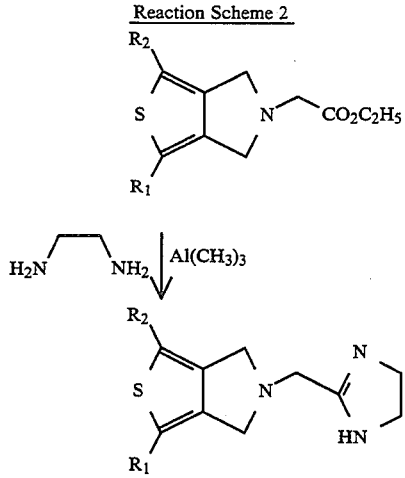

This process consists in reacting a compound of formula (A), in which Y represents a halogen atom, with ethyl 2-aminoacetate, in the presence of potassium carbonate, in a solvent such as dimethylformamide or dimethyl sulphoxide, at room temperature, and in then reacting the ethyl 2-(5,6-dihydro-4H-thieno[3,4-c]pyrrol-5-yl)acetate derivative obtained with ethylenediamine, in the presence of trimethylaluminium, in a solvent such as toluene, at the reflux temperature.

The compound of formula (I) in which $R_3$ represents a 1H-imidazol-4-yl group and $R_1$ and $R_2$ represent hydrogen atoms can also be prepared by reaction of the compound of formula (Ia), in which $R_1$ and $R_2$ are bromine atoms, with ammonium formate in the presence of palladium-on-charcoal, followed by deprotection of the compound of formula (Ia), in which $R_1$ and $R_2$ are hydrogen atoms, thus obtained.

The processes for the preparation of the compounds of formula (II) depend on the nature of the $R_1$ and $R_2$ substituents. These processes are represented in Reaction Schemes 3 to 6 described below:

Reaction Scheme 3

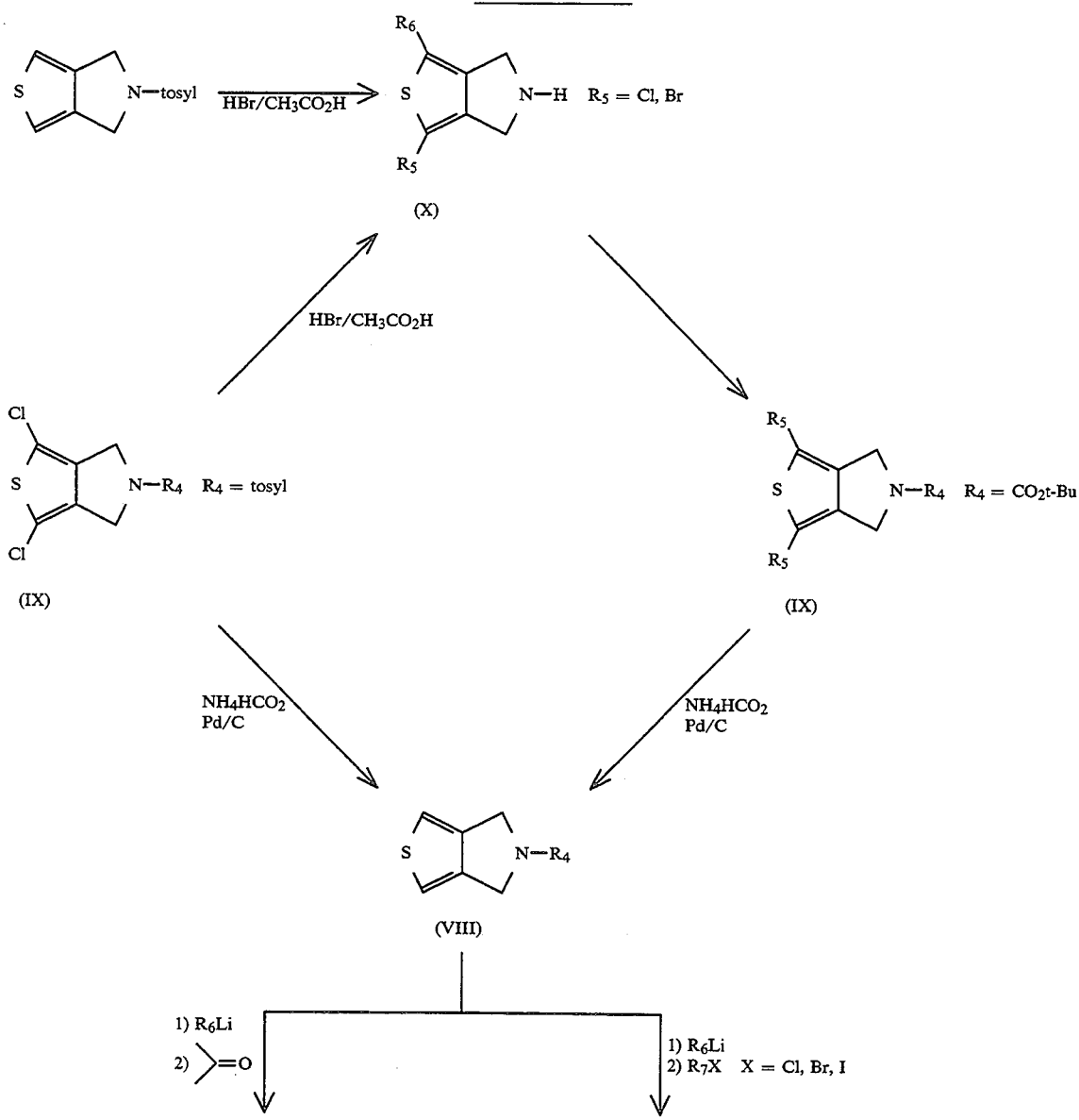

-continued
Reaction Scheme 3

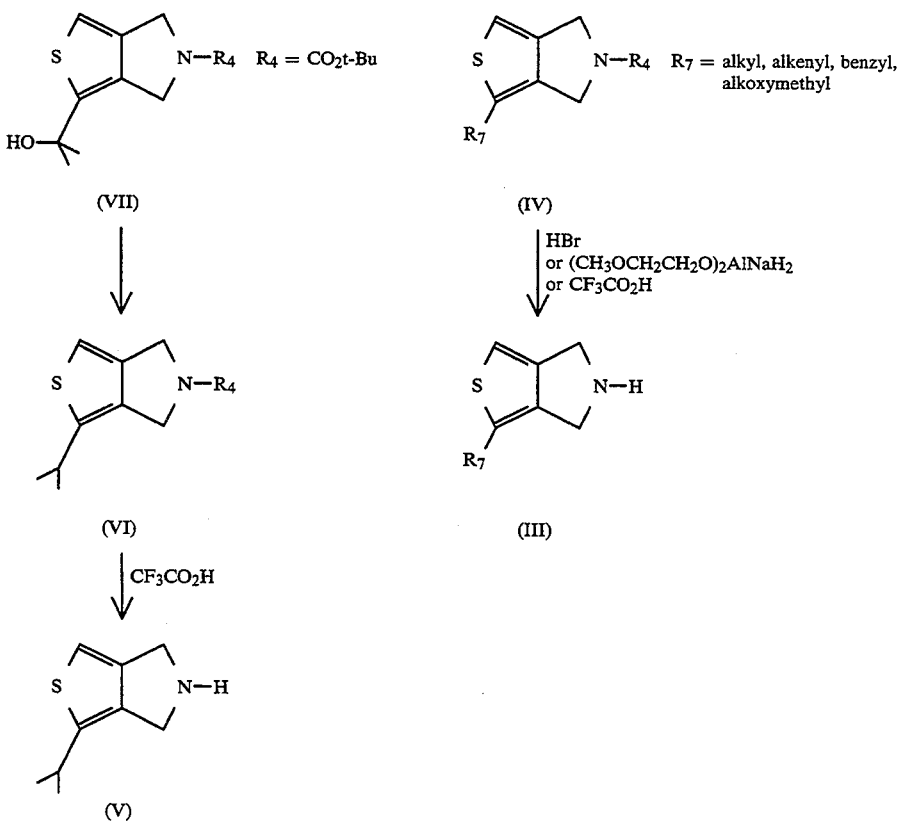

The processes represented in Reaction Scheme 3 relate to the preparation of the compounds of formula (II) in which $R_2$ represents a hydrogen atom and $R_1$ represents an alkyl, alkenyl, benzyl or alkoxymethyl group [compounds of formula (III)] or in which $R_2$ represents a hydrogen atom and $R_1$ represents a branched alkyl group (compound of formula (V) and analogous compounds).

According to one of these processes, a compound of formula (VIII), in which $R_4$ represents a tosyl or t-butoxycarbonyl group, is reacted with a strong base, for example a compound of formula $R_6Li$ in which $R_6$ represents an alkyl or dialkylamino, in particular n-butyl or diisopropylamino, group, in a solvent such as tetrahydrofuran, at a temperature in the region of $-70°$ C., and then with a halide of formula $R_7X$ in which X represents a chlorine, bromine or iodine atom and $R_7$ represents an alkyl, alkenyl, benzyl or alkoxymethyl group to produce a compound of formula (IV), which is then treated with sodium bis(2-methoxy-ethoxy) aluminium hydride, in a solvent such as toluene, at the reflux temperature or with hydrobromic acid at a temperature in the region of 90° C. or with trifluoroacetic acid, at a temperature in the region of 0° C., to give the compound of formula (III).

According to the other process, the compound of formula (VIII), in which $R_4$ represents the t-butoxycarbonyl group, is reacted with a strong base such as $R_6Li$, in which $R_6$ represents a dialkylamino group, and then with acetone to produce the compound of formula (VII) which, treated With acetic acid, in a solvent such as chloroform, in the presence of calcium chloride and then with ammonium formate in the presence of palladium-on-charcoal, gives the compound of formula (VI) which is then treated with trifluoroacetic acid to give the compound of formula (V). The use of another ketone in place of acetone makes it possible to obtain analogous compounds where the isopropyl group is replaced by another branched alkyl group.

The compound of formula (VIII), in which $R_4$ represents the t-butoxycarbonyl group, is obtained by reaction of a compound of formula (X), in which $R_5$ represents a chlorine or bromine atom, with di(1,1-dimethylethyl) dicarbonate and then reaction of the compound of formula (IX), in which $R_4$ represents the t-butoxycarbonyl group, with ammonium formate in the presence of palladium-on-charcoal, in a solvent such as methanol and at a temperature of approximately 65° C.

The compound of formula (VIII), in which $R_4$ represents tosyl, is obtained by reaction of the compound of formula (IX), in which $R_5$ represents a chlorine atom and $R_4$ represents tosyl, with ammonium formate in the presence of palladium-on-charcoal, in a solvent such as methanol and at a temperature of approximately 65° C.

The compounds of formula (X) in which $R_5$ represents a chlorine atom or a bromine atom are obtained by treating 1,3-dichloro-5,6-dihydro-5-tosyl-4H-thieno[3,4-c]pyrrole or 5,6-dihydro-5-tosyl-4H-thieno[3,4-c]pyrrole respectively with hydrobromic acid, in the presence of acetic acid.

Reaction Scheme 4

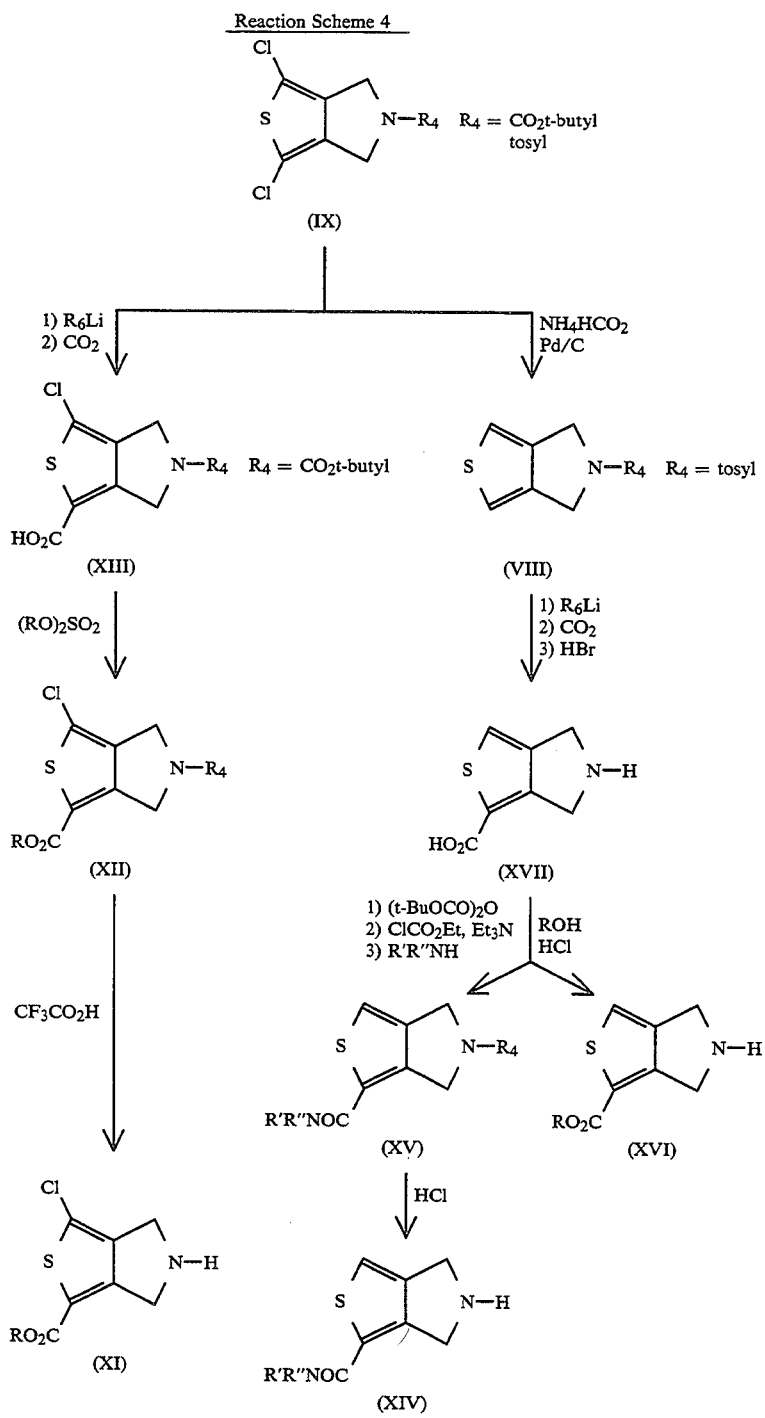

The processes represented in Reaction Scheme 4 relate to the preparation of the compounds of formula (II) in which $R_2$ represents a chlorine atom and $R_1$ represents a $CO_2R$ group [compounds of formula (XI)] or in which $R_2$ represents a hydrogen atom and $R_1$ represents a group $CONR'R''$ or $CO_2R$ [compounds of formulae (XIV) and (XVI)], R, R' and R'' having the meanings shown above.

According to one of these processes, the compound of formula (IX), in which $R_4$ represents the t-butoxycarbonyl group, is reacted with a strong base such as t-butyllithium, in a solvent such as tetrahydrofuran, and then with carbon dioxide to give the compound of formula (XIII), which is then treated with a sulphate of formula $(RO)_2SO_2$, in which R is defined as above, to give the compound of formula (XII) which is treated with trifluoroacetic acid to lead to the compound of formula (XI).

According to the other process, the compound of formula (IX), in which $R_4$ represents tosyl, is converted to the compound of formula (VIII) according to the method shown above and this compound is then treated with a strong base, such as n-butyllithium, in a solvent such as tetrahydrofuran, at a temperature in the region of $-70°$ C., then with carbon dioxide and finally with hydrobromic acid in acetic acid to produce the compound of formula (XVII) which is either treated with di(1,1-dimethylethyl) dicarbonate, then with ethyl chloroformate in the presence of triethylamine and finally with an amine of formula R'R" NH in which R' and R" are defined as above, to give a compound of formula (XV) which then reacts with gaseous hydrochloric acid, in a solvent such as ethyl acetate, at a temperature in the region of 20° C. to give the compound of formula (XIV) or treated with gaseous hydrochloric acid and an alcohol of formula ROH, at a temperature in the region of 70° C., to give the compound of formula (XVI), in which R is defined as above.

temperature in the region of −70° C., and then with water, to produce the compound of formula (XIX).

According to the other process, the compound of formula (IX) is treated with phenylboronic acid, in the presence of palladium(O) as catalyst and of a base such as sodium carbonate, in a solvent such as a toluene/water mixture, at a temperature in the region of 90° C., to produce the compound of formula (XXIII) which is then treated with ammonium formate in the presence of palladium-on-charcoal, in a solvent such as methanol at a temperature in the region of 65° C., to give the compound of formula (XXI). The compounds of formulae (XVIII), (XX) and (XXII) are obtained respectively

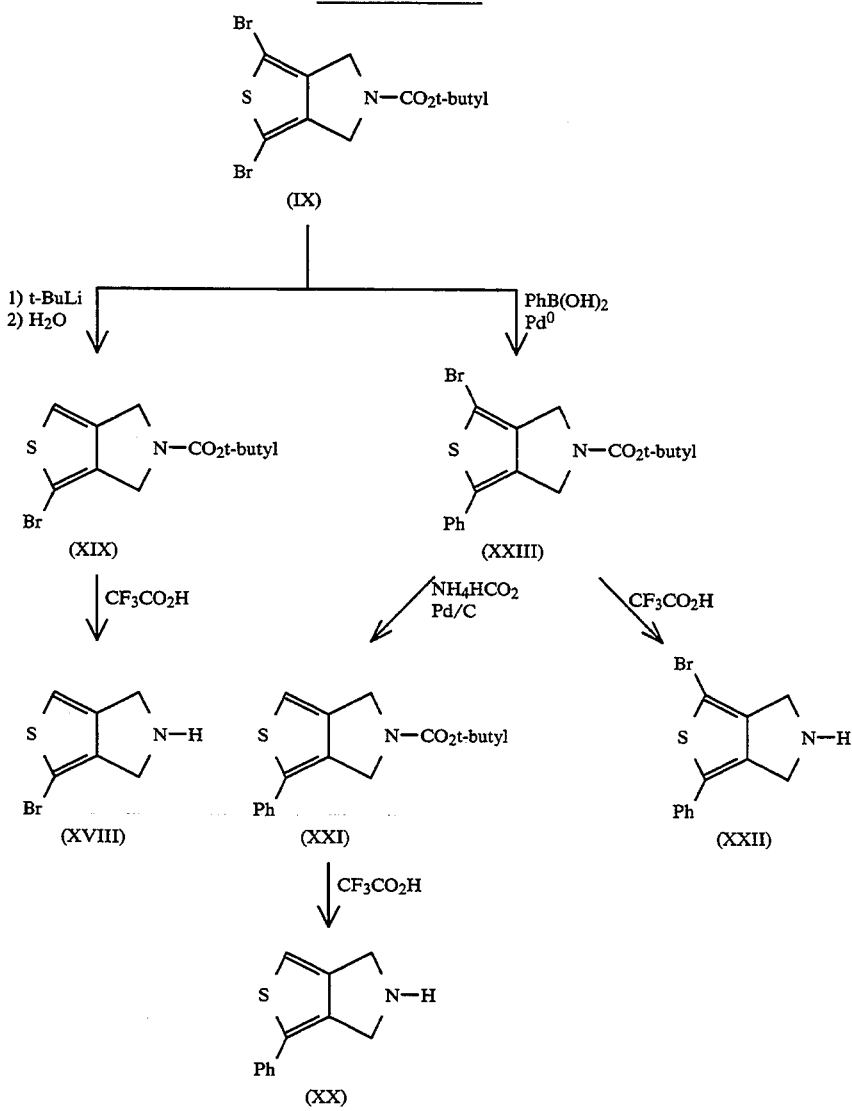

Reaction Scheme 5

The processes represented in Reaction Scheme 5 relate to the preparation of compounds of formula (II) in which one of the $R_1$ or $R_2$ substituents represents a hydrogen atom and the other a bromine atom [compound of formula (XVIII)] or in which $R_2$ represents a hydrogen or bromine atom and $R_1$ represents a phenyl group [compounds of formulae (XX) and (XXII)].

According to one of these processes, the compound of formula (IX) is treated with a strong base, such as t-butyllithium, in a solvent such as tetrahydrofuran, at a from the compounds of formulae (XIX), (XXI) and (XXIII), by reaction with trifluoroacetic acid.

Reaction Scheme 6

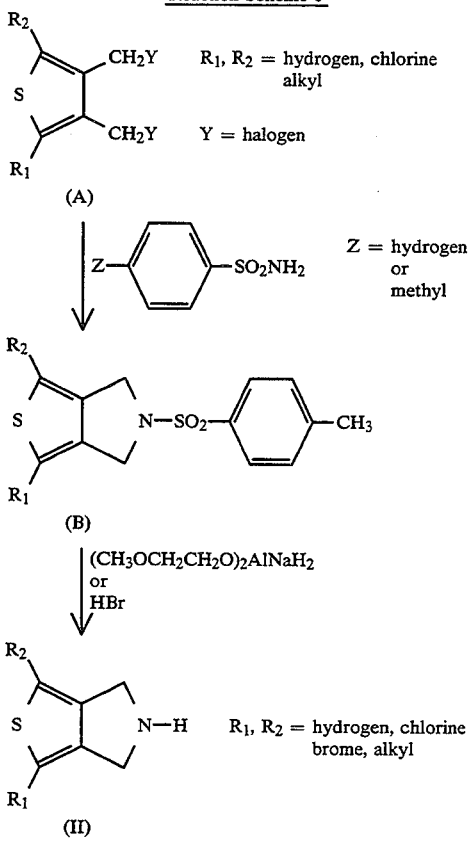

The compounds of formula (II) in which $R_1$ and $R_2$ represent hydrogen, chlorine or bromine atoms or alkyl groups are obtained according to reaction scheme 6. The compound of formula (A), in which Y is a halogen atom and $R_1$ and $R_2$ are hydrogen or chlorine atoms or alkyl groups, is reacted with an arylsulphonamide such as benzenesulphonamide or p-toluenesulphonamide, in a solvent such as dimethylformamide, in the presence of potassium carbonate, at a temperature of approximately 100° C., and then the compound of formula (B) obtained is reacted with sodium bis(2-methoxyethoxy)aluminium hydride, in a solvent such as toluene, at the reflux temperature, or else with hydrobromic acid in acetic acid, at a temperature of approximately 90° C.

The compounds of formula (A) are described in the literature or are prepared by known methods.

The following Examples illustrate the invention. Examples 1 to 5 relate to the preparation of the compounds of formula (II) according to the processes represented in Reaction Schemes 3 to 6. The analyses confirm the structure of the compounds.

EXAMPLE 1:
1-Methyl-5,6-dihydro-4H-thieno[3,4-c]pyrrole hydrobromide.

1.1 5-Tosyl-5,6-dihydro-4H-thieno[3,4-c]pyrrole.

28 g of 10% palladium-on-charcoal containing 50% water and then 96 g (1.52 mol) of ammonium formate are added, under a nitrogen atmosphere, to a solution of 28.34 g (0.81 mol) of 1,3-dichloro-5-tosyl-5,6-dihydro-4H-thieno[3,4-c]pyrrole in 800 ml of methanol. The mixture is heated at reflux for 3 hours, 28 g of wet palladium-on-charcoal are then added and reflux is maintained for 24 hours. After filtration through diatomaceous earth, the filtrate is evaporated to dryness and the residue is recrystallized from methanol. 16.64 g of a white solid are obtained. Yield 73%. Melting point: 125°–127° C.

1.2
1-Methyl-5-tosyl-5,6-dihydro-4H-thieno[3,4-c]pyrrole.

9.4 ml (15 mmol) of a 1.6M solution of butyllithium in hexane are added, at −70° C., to a solution of 3.5 g (12.5 mmol) of 5-tosyl-5,6-dihydro-4H-thieno[3,4-c]pyrrole in 40 ml of dry tetrahydrofuran; after 15 min, 1 ml (16 mmol) of iodomethane is added, the mixture is then stirred at room temperature for 30 min and poured into 200 ml of water. The precipitate formed is filtered and washed with hexane; after purification on silica gel using the 1/9 ethyl acetate/hexane eluent mixture, there are obtained 3.16 g of a white solid. Yield 86%. Melting point: 158°–160° C.

1.3 1-Methyl-5,6-dihydro-4H-thieno[3,4-c]pyrrole hydrobromide.

A mixture of 3.1 g (10.6 mmol) of 1-methyl-5-tosyl-5,6-dihydro-4H-thieno[3,4-c]pyrrole and 3.1 g (32.9 mmol) of phenol in 43 ml of a 33% solution of hydrobromic acid in acetic acid, placed in a sealed tube, is heated at 90° C. in a water bath for 3 hours. The reaction mixture is then filtered and poured into 150 ml of water and then extracted with three times 150 ml of diethyl ether. The aqueous phase is evaporated to dryness and the residue washed with acetone. There is obtained 0.64 g of a pasty solid. Yield 27%.

EXAMPLE 2:
1,3-Dichloro-5,6-dihydro-4H-thieno[3,4-c]pyrrole

A mixture of 6.98 g (0.02 mol) of 1,3-dichloro-5-tosyl-5,6-dihydro-4H-thieno[3,4-c]pyrrole and 50 ml of a 33% solution of hydrobromic acid in acetic acid, placed in a sealed tube, is heated at 90° C. in a water bath for 90 min. The reaction mixture is then cooled, and the precipitate formed is filtered off, washed twice with diethyl ether and dried. There are obtained 4.75 g of compound in the hydrobromide form (Melting point >270° C.). Treatment of this salt with sodium carbonate in water produces 3.35 g of base. Melting point: 80.5°–82.5° C.

EXAMPLE 3:
1-Bromo-3-phenyl-5,6-dihydro-4H-thieno-[3,4-c]pyrrole trifluoroacetate.

3.1 1,3-Dibromo-5,6-dihydro-4H-thieno[3,4-c]pyrrole hydrobromide.

A mixture of 5.5 g (0.019 mol) of 5-tosyl-5,6-dihydro-4H-thieno[3,4-c]pyrrole and 60 ml of a 33% solution of hydrobromic acid in acetic acid is heated at 90° C. for 1 h. The mixture is then cooled, and the precipitate formed filtered off, washed twice with diethyl ether and dried. There are obtained 4.6 g of product. Melting point: >270° C.

3.2
1,3-Dibromo-5-(1,1-dimethylethoxy)carbonyl-5,6-dihydro-4H-thieno[3,4-c]pyrrole.

A solution of 0.9 g (4.12 mmol) of di(1,1-dimethylethyl)dicarbonate in 3.5 ml of dioxane followed by 4 ml of a 2M sodium hydroxide solution are added dropwise and at 0° C. to a suspension of 1 g (2.74 mmol) of 1,3-dibromo-5,6-dihydro-4H-thieno[3,4-c]pyrrole hydrobromide in 6.5 ml of dioxane. After stirring for 1 hour at room temperature, the precipitate is filtered off, rinsed with twice 5 ml of water, and dried at 70° C. There is obtained 0.95 g of a white solid. Yield 91%. Melting point: 144°–145° C.

3.3
1-Bromo-3-phenyl-5-(1,1-dimethylethoxy)carbonyl-5,6-dihydro-4H-thieno[3,4-c]pyrrole.

0.91 g (7.5 mmol) of phenylboronic acid, 0.209 g (0.38 mmol) of (dibenzylideneacetone)-palladium(O), 0,397 g (1.5 mmol) of triphenylphosphine and 7.5 ml (15 mmol) of a 2M sodium carbonate solution are added to a solution of 3.2 g (8.3 mmol) of 1,3-dibromo-5-(1,1-dimethylethoxy)carbonyl-5,6-dihydro-4H-thieno[3,4-c]pyrrole in 45 ml of toluene. The mixture is heated at reflux for 5.5 hours and then cooled. The organic phase is separated by settling, washed with water, dried over magnesium sulphate and then evaporated to dryness. The residue is purified by chromatography on silica gel using the 5/95 ethyl acetate/hexane eluent mixture. There is obtained 0.98 g of a white solid. Yield 34%. Melting point: 139°–140° C.

3.4
1-Bromo-3-phenyl-5,6-dihydro-4H-thieno[3,4-c]pyrrole trifluoroacetate.

1.5 ml of trifluoroacetic acid are added to 0.98 g (1.32 mmol) of 1-bromo-3-phenyl-5-(1,1-dimethylethoxy)carbonyl-5,6-dihydro-4H-thieno[3,4-c]pyrrole. After 10 minutes at room temperature, the solvent is evaporated to dryness. 5 ml of toluene are added and the mixture is evaporated to dryness. The residue is triturated with 5 ml of diethyl ether, filtered and dried. There is obtained 0.95 g of a yellowish solid. Yield 91%.

EXAMPLE 4:
1,3-Dimethyl-5,6-dihydro-4H-thieno[3,4-c]pyrrole.

4.1
1,3-Dimethyl-5-tosyl-5,6-dihydro-4H-thieno[3,4-c]pyrrole.

A solution of 10 g (0.048 mol) of 3,4-bis(chloromethyl)-2,5-dimethylthiophene and 8.22 g of p-toluenesulphonamide in 600 ml of dry dimethylformamide is added dropwise, over 6 h, to a stirred suspension, heated to 100°–110° C., of 180 g of potassium carbonate in 900 ml of dimethylformamide. After the end of the addition, the mixture is maintained at the same temperature for 30 min, and then filtered. The solid is washed with dimethylformamide. The filtrate is concentrated under vacuum, and the residue is treated with 100 ml of ethanol, and filtered. The solid residue remaining is washed with ethanol and dried. 9.39 g of product are obtained. Melting point: 163°–164° C.

4.2 1,3-Dimethyl-5,6-dihydro-4H-thieno[3,4-c]pyrrole.

A mixture of 38 ml of a 3.4M solution of sodium bis(2-methoxyethoxy)aluminium hydride in toluene and 10 ml of dry toluene is added, at room temperature, to a suspension of 9.1 g (0.03 mol) of 1,3-dimethyl-5-tosyl-5,6-dihydro-4H-thieno [3,4-c]pyrrole in 42 ml of dry toluene. The mixture is then heated at reflux for 2 h 30 min, cooled to room temperature, and poured into 400 ml of 1N sodium hydroxide. The organic phase is washed with 3 times 50 ml of water and extracted with a 0.5N hydrochloric acid solution. The solid, precipitated by addition of a sodium carbonate solution, is filtered off, washed with water and dried. 3.12 g of product are obtained. Melting point: 110°–112° C. (with decomposition).

EXAMPLE 5:
1-(1-Methylethyl)-5,6-dihydro-4H-thieno[3,4-c]pyrrole trifluoroacetate.

5.1
1,3-Dichloro-5-(1,1-dimethylethoxy)carbonyl-5,6-dihydro-4H-thieno[3,4-c]pyrrole.

A solution of 61.64 g (282 mmol) of di(1,1-dimethylethyl) dicarbonate in 275 ml of dioxane followed by 274 ml of a 2M sodium hydroxide solution are added dropwise, at 0° C., to a suspension of 50 g (182 mmol) of 1,3-dichloro-5,6-dihydro-4H-thieno[3,4-c ]pyrrole hydrobromide in 500 ml of dioxane. After stirring for 1 hour at room temperature, the precipitate is filtered off, rinsed with twice 500 ml of water and dried at 70° C. 51 g of a white solid are obtained. Yield 95%. Melting point: 112°–114° C.

5.2
5-(1,1-Dimethylethoxy)carbonyl-5,6-dihydro-4H-thieno[3,4-c]pyrrole.

17.6 g of 10% palladium-on-charcoal containing 50% of water and then 41.6 g (600 mmol) of ammonium formate are added to a solution of 8.82 g (30 mmol) of 1,3-dichloro-5(1,1-dimethylethoxy)-carbonyl-5,6-dihydro-4H -thieno[3,4-c]pyrrole in 75 ml of methanol. The mixture is heated at reflux for 24 hours and it is then cooled, filtered through a Celite column, rinsed with twice 50 ml of dichloromethane and evaporated to dryness. The residue is taken up in 100 ml of dichloromethane, filtered and evaporated to dryness. There are obtained 4.54 g of an oily product which crystallizes slowly. Yield 68%. Melting point: 36°–38° C.

5.3
1-(2-Hydroxy-2-propyl)-5-(1,1-dimethylethoxy)-carbonyl-5,6-dihydro-4H-thieno[3,4-c]pyrrole.

3.15 ml (5 mmol) of a 1.6M solution of butyllithium in hexane are added, at 0° C., to a solution of 0.7 ml (5 mmol) of N,N-diisopropylamine in 20 ml of dry tetrahydrofuran. After 30 min, the mixture is cooled to −70° C. and a solution of 0.95 g (4.2 mmol) of 5-(1,1-dimethylethoxy)carbonyl-5,6-dihydro-4H-thieno[3,4-c]pyrrole in 15 ml of tetrahydrofuran is added. After 1 hour at −70° C., 1.54 ml (21 mmol) of acetone are added and the mixture is then stirred at room temperature overnight. The reaction mixture is poured into 50 ml of water and then extracted with three times 30 ml of dichloromethane; the organic phases are dried over sodium sulphate and then evaporated to dryness. The residue is chromatographed on a column of silica gel using the ¼ ethyl acetate/cyclohexane eluent mixture. 0.425 g of a white solid is obtained. Yield 36%. Melting point: 113.5° C.

5.4
1-(1-Propen-2-yl)-5-(1,1-dimethylethoxy)carbonyl-5,6-dihydro-4H-thieno[3,4-c]pyrrole.

5 g of calcium chloride and 0.17 ml (3 mmol) of acetic acid are added to a solution of 0.81 g (2.86 mmol) of 1-(2-hydroxy-2-propyl)-5-(1,1-dimethyl-ethoxy) carbonyl-5,6-dihydro-4H-thieno[3,4-c]pyrrole in 60 ml of chloroform. The mixture is heated at reflux for 24 hours, filtered, washed with a 5% sodium bicarbonate solution, then dried over sodium sulphate and evaporated to dryness. 0.78 g of an oily product is obtained.

5.5
1-(1-Methylethyl)-5-(1,1-dimethylethoxy)carbonyl-5,6-dihydro-4H-thieno[3,4-c]pyrrole.

3.7 g (59 mmol) of ammonium formate and then 0.9 g of 10% palladium-on-charcoal are added to a solution of 0.78 g (2.9 mmol) of 1-(1-propen-2-yl)-5-(1,1-dimethylethoxy)carbonyl-5,6-dihydro-4H-thieno[3, 4-c]pyrrole in 40 ml of methanol. The reaction mixture is heated at reflux for 8 hours, then filtered on a Celite column and evaporated to dryness. The residue is taken up in 50 ml of ethyl acetate, washed with 20 ml of water, dried over sodium sulphate and evaporated to dryness. After purification on a silica column using the ¼ ethyl acetate/hexane eluent mixture, 0.49 g of an oily product is obtained. Yield 63%.

5.6
1-(1-Methylethyl)-5,6-dihydro-4H-thieno[3,4-c]pyrrole trifluoroacetate.

A solution of 0.49 g (1.8 mmol) of 1-(1-methylethyl)5-(1,1-dimethylethoxy)carbonyl-5,6-dihydro -4H-thieno[3,4-c]pyrrole in 0.5 ml of trifluoroacetic acid is stirred for 30 min at a temperature in the region of 20° C. After evaporation of the solvent, 0.51 g of an oily product is obtained. Quantitative yield.

EXAMPLE 6:
1,3-Dichloro-5-[(4,5-dihydro-1H-imidazol-2-yl)methyl]-5,6-dihydro-4H-thieno [3,4-c]pyrrole dihydrochloride.

A solution of 2.13 g (0.011 mol) of 1,3-dichloro-5,6-dihydro-4H-thieno[3,4-c]pyrrole and 2.5 ml of N,N-diisopropylethylamine in 25 ml of dimethylformamide is poured onto a mixture of 1.95 g (0.0125 mol) of 2-chloromethyl-1H-4,5-dihydroimidazole hydrochloride, 2.5 ml of N,N-diisopropylethylamine and 25 ml of dimethylformamide. The mixture is subjected to ultrasound for 8 h and is then evaporated under vacuum. The residue is dissolved in 75 ml of salt solution and extracted with 5 times 50 ml of methylene chloride. The organic solution is dried and then concentrated to produce a residue which is dissolved in 50 ml of isopropanol and treated with 14 ml of a 1N solution of hydrochloric acid in isopropanol. The crystals formed by cooling are filtered and washed with diethyl ether. 0.5 g of product is obtained. Melting point: 206°–213° C. (with decomposition).

EXAMPLE 7:
5-[(4,5-Dihydro-1H-imidazol-2-yl)methyl]-5,6-dihydro-4H-thieno[3,4-c]pyrrole hydrochloride.

7.1 Ethyl 2-(5,6-dihydro-4H-thieno[3,4-c]pyrrol-5yl)acetate.

13.18 g (0.0945 mol) of ethyl aminoacetate hydrochloride, 33.8 g (0.245 mol) of potassium carbonate and 60 ml of dimethylformamide are introduced, under argon, into a 250 ml round-bottomed flask. The mixture is cooled to 5° C. and 8.5 g (0.0315 mol) of 3,4bis(bromomethyl)thiophene in solution in 30 ml of dimethylformamide are added over 25 minutes. This mixture is stirred at room temperature for 67 h. The mixture is poured into 500 ml of ice-cold water and extracted 3 times with ether. The organic phases are washed 3 times with water, combined, dried, filtered and then concentrated under reduced pressure. There are obtained 1.57 g (0.007 mol) of product (yield 24%).

7.2 5-[(4,5-Dihydro-1H-imidazol-2-yl)methyl]-5,6-dihydro-4H-thieno[3,4-c]pyrrole hydrochloride.

17 ml of toluene and 8.9 ml (0.0213 mol) of a 25% solution of trimethylaluminium in hexane are introduced, under argon, into a 150 ml, three-necked, round-bottomed flask. The mixture is cooled using ice and 1.28 g (0.0213 mol) of ethylenediamine in solution in 5 ml of toluene are added dropwise. The reaction mixture is heated to 60° C. and 1.5 g (0.0071 mol) of ethyl 2-(5,6-dihydro-4H-thieno[3,4c]pyrrol-5-yl)acetate in solution in 17 ml of toluene are introduced. The mixture is brought to the reflux temperature, 15 ml of solvent are distilled and the mixture is kept at boiling point for 1 h 30. After cooling, the temperature of the mixture is brought to −10° C., 10 ml of water, 40 ml of dichloromethane and 20 ml of ethyl acetate are added and the mixture is stirred for 30 minutes. The suspension is poured into 100 ml of ethyl acetate, washed with water, dried and evaporated under reduced pressure. A solid product (0.9 g) is obtained which is converted to the hydrochloride using a 0.1N solution of hydrochloric acid in isopropanol. Recrystallization is carried out from a mixture of isopropanol and ethyl acetate (4/1). 0.5 g (0.002 mol) of a white solid is obtained (yield: 28%). Melting point: 212°–215° C.

EXAMPLE 8:
1,3-Dibromo-5-[(4,5-dihydro-1H-imidazol-2-yl)methyl]-5,6-dihydro-4H-thieno[3, 4-c]pyrrole.

A solution of 1.82 g (0.005 mol) of 1,3-dibromo-5,6-dihydro-4H-thieno[3,4-c]pyrrole hydrobromide and 2.5 ml of N,N-diisopropylethylamine in 25 ml of dimethylformamide is poured onto a mixture of 1.15 g (0.0073 mol) of 2-chloromethylimidazoline hydrochloride, 1 ml of N,N-diisopropylethylamine and 25 ml of dimethylformamide. The reaction mixture is subjected to ultrasound for 12 h and is then evaporated under vacuum. The residue is dissolved in 75 ml of salt solution and then extracted with 5 times 30 ml of methylene chloride. The organic solution is dried and concentrated to give a residue which is dissolved in 50 ml of water. The precipitate formed by addition of 5N sodium hydroxide solution is washed with water. 1.3 g of compound are obtained. Melting point: 175° C. (with decomposition).

EXAMPLE 10:
1-Chloro-5-[(4,5-dihydro-1H-imidazol-2-yl)methyl]-5,6-dihydro-4H-thieno[3, 4-c]pyrrole dihydrochloride.

10.12-Chloro-3,4-bis(hydroxymethyl)thiophene.

20 g (0.095 mol) of 2,5-dichloro-3,4-bis(hydroxymethyl)thiophene are poured onto a suspension of 20 g of 10% palladium-on-charcoal in 500 ml of methanol, in which 20 g (0.35 mol) of potassium hydroxide have been dissolved. The mixture is stirred and heated at reflux while passing a stream of hydrogen through. At the end of 24 h, the mixture is filtered, the filtrate is concentrated, the residue is poured into 50 ml of cold water and extracted with twice 100 ml and then 6 times 50 ml of diethyl ether. The ether phases are dried over magnesium sulphate and concentrated. 8.49 g of product are obtained. Melting point: 68°–69° C.

10.2 2-Chloro-3,4-bis(bromomethyl)thiophene.

A solution of 20 ml of phosphorus tribromide in 75 ml of carbon tetrachloride is poured, over 30 min, onto a mixture of 8.29 g (0.0464 mol) of 2-chloro-3,4-bis(hydroxymethyl)thiophene and 300 ml of carbon tetrachloride, cooled in a water bath. The mixture is then stirred for 1 h, at room temperature, and 175 ml of cold water are added. The organic phase is separated, washed with 50 ml of 10% sodium bicarbonate and 100 ml of water, and dried over magnesium sulphate. The solution is concentrated to produce 12.94 g of an oily product which is used as is in the following stage.

10.3 Ethyl 2-(1-chloro-5,6-dihydro-4H-thieno[3,4-c]pyrrol-5-yl)acetate.

A solution of 12.58 g (0.041 mol) of 2-chloro-3,4-bis(bromomethyl)thiophene in 40 ml of dimethylformamide is poured dropwise onto a mixture of 17.77 g of ethyl 2-aminoacetate hydrochloride, 45.5 g of finely powdered potassium carbonate and 80 ml of dimethylformamide, cooled to 5° C. The mixture is stirred at room temperature for 2 h, then poured onto 400 g of a water-/ice mixture and stirred for a further 15 min. The mixture is extracted with 5 times 100 ml of diethyl ether, the ether phase is washed with twice 100 ml of salt solution, dried over magnesium sulphate and concentrated. 9.49 g of an oily product are obtained.

10.4 1-Chloro-5-[(4,5-dihydro-1H-imidazol-2-yl)methyl]5,6-dihydro-4H-thieno[3,4-c]pyrrole dihydrochloride.

A solution of 6.85 g (0.114 mol) of ethylenediamine in 30 ml of toluene is poured dropwise onto a mixture of 90 ml of dry toluene and 57 ml (0.114 mol) of trimethylaluminium as a 2M solution in toluene cooled to 0° C. The mixture is then heated to 60° C. in an oil bath and then a solution of 9.38 g (0.038 mol) of ethyl 2-(1-chloro-5,6-dihydro-4H-thieno[3,4-c]pyrrol-5-yl)acetate in 90 ml of toluene is added. The mixture is heated at reflux for 1 h 30 min, is then cooled to $-10°$ C. and hydrolyzed with 60 ml of water while maintaining the temperature between $-10°$ C. and $+5°$ C. 250 ml of methylene chloride and 150 ml of ethyl acetate are added, the inorganic salts are removed by filtration, the organic phase is separated, washed with 3 times 250 ml of water, dried and concentrated under vacuum. There are obtained 4.41 g of product which is dissolved in 75 ml of isopropanol and treated with 40 ml of a 1M solution of hydrochloric acid in isopropanol. The solution is concentrated and the product is recrystallized from 45 ml of ethanol. 4.50 g of product are obtained. Melting point: 217°–219° C. (with decomposition).

EXAMPLE 11:
1-Ethoxycarbonyl-5-[(4,5-dihydro-1H-imidazol-2-yl)methyl]-5,6-dihydro-4H-thieno [3,4-c]pyrrole dihydrochloride.

11.1 1-Carboxy-5-tosyl-5,6-dihydro-4H-thieno[3,4-c]pyrrole.

9.4 ml (15 mmol) of a 1.5M solution of butyllithium in hexane are added, under argon and at $-70°$ C., to a solution of 3.5 g (12.5 mmol) of 5-tosyl-5,6-dihydro-4H-thieno[3,4c]pyrrole in 40 ml of dry tetrahydrofuran. After 10 minutes, the mixture is poured onto 200 g of solid carbon dioxide and then evaporated to dryness. 50 ml of water are added and the suspension obtained is filtered and then poured onto 1M hydrochloric acid. A precipitate is obtained which is filtered and dried to provide 2.85 g of a cream solid. Yield 70%. Melting point: 234°–236° C. (with decomposition).

11.2 1-Carboxy-5,6-dihydro-4H-thieno[3,4-c]pyrrole hydrobromide.

A mixture of 0.5 g (1.54 mmol) of 1-carboxy-5-tosyl-5,6-dihydro-4H-thieno[3,4-c]pyrrole and 5 ml of a 33% solution of hydrobromic acid in acetic acid, placed in a sealed tube, is heated at 60° C. in a water bath for 15 min. The reaction mixture is then cooled, the precipitate formed is filtered, washed twice with diethyl ether and dried. 0.32 g of product is obtained in the hydrobromide form. Yield 83%. Melting point: 281.3°–281.7° C.

11.3 1-Ethoxycarbonyl-5,6-dihydro-4H-thieno-[3,4-c]pyrrole hydrochloride.

A stream of hydrochloric acid is passed into a suspension of 3.3 g (13.2 mmol) of 1-carboxy-5,6-dihydro-4H-thieno[3,4-c]pyrrole hydrobromide in 75 ml of ethanol, heated at reflux for 4 h. The solvent is then evaporated and the residue triturated with twice 20 ml of diethyl ether. 2.46 g of a beige solid are obtained. Yield 80%. Melting point: 163° C. (with decomposition).

11.4 1-Ethoxycarbonyl-5-[(4,5-dihydro-1H-imidazol-2yl)methyl]-5,6-dihydro-4H-thieno[3, 4-c]pyrrole dihydrochloride.

A solution of 0.65 g of 1-ethoxycarbonyl-5,6-dihydro-4h-thieno[3,4-c]pyrrole hydrochloride and 1.47 ml of N,N-diisopropylethylamine in 15 ml of dimethylformamide is poured onto a mixture of 0.75 g of 2-chloromethyl-1H-4,5dihydroimidazole hydrochloride, 0.5 ml of N,N-diisopropylethylamine and 15 ml of dimethylformamide. The mixture is subjected to ultrasound for 4 h and is then evaporated under vacuum. The residue is dissolved in 3 ml of ethanol and chromatography is carried out on a silica column with ethanol as eluent. After evaporating the solvent, the residue is treated with 5 ml of isopropanol saturated with hydrochloric acid. 0.182 g of product is obtained. Melting point: 213°–215° C. (with decomposition).

EXAMPLE 12:
1-Ethyl-5-[(4,5-dihydro-1H-imidazol-2yl)methyl]-5,6-dihydro-4H-thieno[3,4-c]pyrrole dihydrochloride.

12.1 1-Ethyl-5-tosyl-5,6-dihydro-4H-thieno[3,4-c]pyrrole 3.75 ml of a 1.6M solution of n-butyllithium in hexane are added, at $-70°$ C., to a solution of 1.4 g of 5-tosyl-5,6-dihydro-4H-thieno[3,4-c]pyrrole in 15 ml of dry tetrahydrofuran. 0.51 ml of iodoethane is then added and the mixture is stirred at room temperature for 2 h and the solution is then poured into 100 ml of ice-cold water. The solid formed is filtered off, washed with hexane and recrystallized from ethanol. 0.16 g of product is obtained. Melting point: 117°–120° C.

12.2 1-Ethyl-5,6-dihydro-4H-thieno[3,4-c]pyrrole hydrochloride.

20 ml of a 3.4M solution of sodium bis(2-methoxyethoxy)aluminium hydride in toluene are poured at room temperature onto a solution of 4.8 g of 1-ethyl-5-tosyl-5,6-dihydro-4H-thieno[3,4-c]pyrrole in 50 ml of dry toluene. The mixture is heated at reflux for 26 h, then cooled to room temperature and poured into 300 ml of 1N sodium hydroxide. The organic phase is washed with 3 times 10 ml of water and then evaporated to dryness. The residue is dissolved in 5 ml of isopropanol saturated with hydrochloric acid. The crystals formed are then filtered off, washed with acetone and dried. 0.3 g of product is obtained. Melting point: 149°-151° C.

12.3
1-Ethyl-5-[(4,5-dihydro-1H-imidazol-2-yl)methyl]-5,6-dihydro-4H-thieno[3,4-c]pyrrole dihydrochloride 0.53 g of 1-ethyl-5,6-dihydro-4H-thieno-[3,4-c]pyrrole hydrochloride, 1.47 ml of N,N-diisopropylethylamine and 15 ml of dimethylformamide are introduced into a 25 ml round-bottomed flask and then a solution of 0.75 g of 2-chloromethyl-1H-4,5-dihydroimidazole hydrochloride and 0.5 ml of N,N-diisopropylethyl-amine in 15 ml of dimethylformamide is added. The reaction mixture is subjected to ultrasound for 8 h, the solvent is then evaporated and the residue is purified by chromatography on silica gel with ethanol as eluent. The product is recrystallized from 5 ml of isopropanol saturated with hydrochloric acid. 0.233 g of product is obtained. Melting point: 207°-208° C. (with decomposition).

EXAMPLE 13:
1,3-Dibromo-5-[(1H-imidazol-4-yl)methyl]-5,6-dihydro-4H-thieno[3,4-c]pyrrole dihydrochloride.

13.1
1,3-Dibromo-5-[(1-triphenylmethyl-1H-imidazol-4-yl)methyl]-5,6-dihydro-4H-thieno[3, 4-c]pyrrole.

1.5 g (4.1 mmol) of 1,3-dibromo-5,6-dihydro-4H-thieno[3,4-c]pyrrole hydrobromide, 2.12 g (5.9 mmol) of 1-triphenylmethyl-4-chloromethylimidazole, 30 ml of dimethylformamide and 1.54 ml (9 mmol) of N,N-diisopropylethylamine are introduced into a 50 ml round-bottomed flask. The reaction mixture is subjected to ultrasound for 2 hours and is then poured onto ice. The precipitate obtained is filtered, washed with water, taken up in 50 ml of ethyl acetate, dried over sodium sulphate, filtered and evaporated to dryness. The residue is purified by chromatography on silica gel using the 1/1 ethyl acetate/hexane eluent mixture. 0.8 g of a white solid is obtained. Yield 32%.

13.2
1,3-Dibromo-5-[(1H-imidazol-4-yl)methyl]-5,6-dihydro-4H-thieno[3,4-c]pyrrole dihydrochloride.

A suspension of 0.7 g (1.15 mmol) of 1,3-dibromo-5[(1-triphenylmethyl-1H-imidazol-4-yl) methyl]-5,6-dihydro-4H-thieno[3,4-c]pyrrole in 14 ml of 2M hydrochloric acid is heated at reflux for 1 hour. The precipitate formed is filtered and washed with water. The combined aqueous phases are washed with ethyl acetate and then evaporated to dryness to provide 0.45 g of a chestnut-brown solid which is crystallized from isopropanol. 0.082 g of a cream solid is obtained. Yield 17%. Melting point: 221° C. (with decomposition).

EXAMPLE 14:
5-[(1H-Imidazol-4-yl)methyl]-5,6-dihydro-4H-thieno[3,4-c]pyrrole dihydrochloride.

14.1
5-[(1-Triphenylmethyl-1H-imidazol-4-yl)methyl]-5,6-dihydro-4H-thieno[3,4-c]pyrrole.

0.88 g (1.45 mmol) of 1,3-dibromo-5-[(1-triphenylmethyl-1H-imidazol-4-yl)methyl]-5,6-dihydro-4H-thieno3,4-c]pyrrole and 70 ml of methanol are introduced into a 100 ml round-bottomed flask. 1.83 g (29 mmol) of ammonium formate and 0.6 g of 10% palladium-on-charcoal are added to the suspension obtained. The mixture is heated at reflux for 8 hours, then cooled and filtered on Celite. The residue is washed with twice 10 ml of dichloromethane and the filtrates are evaporated to dryness. There is obtained 0.34 g of a solid which is purified by chromatography on silica gel using the 29/1 dichloromethane/methanol eluent mixture. 0.14 g of compound is obtained with a yield of 23%.

14.2
5-[(1H-Imidazol-4-yl)methyl]-5,6-dihydro-4H-thieno[3,4-c]pyrrole dihydrochloride.

0.14 g (0.3 mmol) of 5-[(1-triphenylmethyl-1H-imidazol-4-yl)methyl]-5,6-dihydro-4H -thieno-[3,4-c]pyrrole is dissolved in 1 ml of ethanol, 1.5 ml of 2M hydrochloric acid is then added and the mixture is heated at reflux for 1 hour. The precipitate formed is filtered and the filtrate is washed with twice 1 ml of ethyl acetate and then evaporated to dryness. The residue is dissolved in 2 ml of methanol and decoloured with active charcoal and then recrystallized from isopropanol. There is obtained 0.075 g of cream-white solid in a yield of 86%. Melting point: 260° C.

Compounds of the invention are listed in Tables I and II below with their physical characteristics.

TABLE I

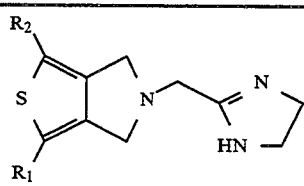

(I)

| Compound | R₁ | R₂ | Base or salt | M.p. (°C.) |
|---|---|---|---|---|
| 1 | CH₃ | H | dihydrochloride | 208–210 (d) |
| 2 | CH₂CH₃ | H | dihydrochloride | 207–208 (d) |
| 3 | (CH₂)₂CH₃ | H | dihydrochloride | 186–189 (d) |
| 4 | (CH₂)₃CH₃ | H | dihydrochloride | 196–198 (d) |
| 5 | CH(CH₃)₂ | H | dihydrochloride | 213 (d) |
| 6 | CH₂CH=CH₂ | H | dihydrochloride | >270 (d) |

TABLE I-continued (I) [Structure: thiophene fused pyrrolidine with R1, R2 substituents, N-CH2-C(=N)-NH- imidazoline group]

| Compound | R1 | R2 | Base or salt | M.p. (°C.) |
|---|---|---|---|---|
| 7 | [phenyl-CH2—] | H | dihydrochloride | 196–199 (d) |
| 8 | Br | H | dihydrochloride | 211–213 (d) |
| 9 | [phenyl-] | Br | dihydrochloride | 245–247 (d) |
| 10 | [phenyl-] | H | dihydrochloride | 209 (d) |
| 11 | $CH_2OCH_3$ | H | dihydrochloride | >270 (d) |
| 12 | $CO_2C_2H_5$ | H | dihydrochloride | 171–174 (d) |
| 13 | $CO_2iC_3H_7$ | H | dihydrochloride | 179–181 (d) |
| 14 | $CO_2C_2H_5$ | Cl | dihydrochloride | 213–215 (d) |
| 15 | $CONHCH_3$ | H | dihydrochloride | 220 (d) |
| 16 | F | H | dihydrochloride | 203–204 |
| 17 | $CO_2CH_2$—[phenyl] | H | dihydrochloride | 195–199 (d) |
| 18 | $CO_2$—[phenyl] | H | dihydrochloride | 211–214 (d) |
| 19 | H | H | hydrochloride | 212–215 |
| 20 | $CH_3$ | $CH_3$ | dihydrochloride | 237–238 |
| 21 | Cl | Cl | dihydrochloride | 206–213 |
| 22 | Br | Br | base | 175 (d) |
| 23 | Cl | H | dihydrochloride | 217–219 (d) |

(d) = decomposition

TABLE II

[Structure: thiophene fused pyrrolidine with R1, R2 substituents, N-CH2-imidazole group]

| Compound | R1 | R2 | Base or salt | M.p. (°C.) |
|---|---|---|---|---|
| 24 | H | H | dihydrochloride | 260 (d) |
| 25 | Br | Br | dihydrochloride | 221 (d) |
| 26 | Cl | Cl | dihydrochloride | 229–231 (d) |
| 27 | Cl | H | dihydrochloride | 241–243 (d) |

(d) = decomposition

The compounds of the invention have an $\alpha_2$-antagonist pharmacological activity demonstrated in the following biological tests.

1. Antagonism of the effects of clonidine on rat vas deferens.

This determination took place on rat vas deferens stimulated at a frequency of 0.1 Hz in the presence of 30 nanomoles of prazosin and of one micromole of cocaine according to the method described by G. M. Drew in European Journal of Pharmacology, 42, 123–130 (1977). The $pA_2$ values of the compounds of the invention are between 6.5 and 9.4.

2. Antagonism of the bonding of $^3$H-clonidine to $\alpha_2$-adrenergic receptors.

The test is carried out on a preparation of rat brain membranes, according to the method described by D. A. Greenberg et al. in Life Sci., 19, 69 (1976). After incubating for 30 min in the-presence of tritiated clonidine (0.05 to 7 nmole/l), the preparation is filtered and the radioactivity of the residue is counted according to the method of P. B. M. W. M. Timmermans et al., described in European Journal of Pharmacology, 70, 7 (1981).

The inhibitory concentrations 50 of the compounds of the invention are between 0.02 and 3.02 μmol/l.

The results of the biological tests show that the compounds of the invention have in vitro antagonist properties with respect to $\alpha_2$-type adrenergic receptors. The compounds of the invention can be used, taking into account their pharmacological properties, for treating diabetes, obesity, hypotension, post-operatory paralytic ileus and/or asthma.

The compounds of the invention also have an $\alpha_1$-agonist activity, revealed by biological tests on the isolated rabbit pulmonary artery.

These tests were carried out under the following conditions: rabbits (Fauve de Bourgogne), weighing 2 to 3 kg, were stunned and exsanguinated and their pulmonary arteries were withdrawn, dissected and cut into strips with a width of approximately 1.2 to 2 mm and a length of approximately 20 mm.

These strips of vascular tissue were immersed in a physiological solution (composition, expressed in mmol/l: sodium chloride 137; potassium chloride 2.7; calcium chloride 1.8; sodium dihydrogenphosphate 0.4; sodium hydrogencarbonate 11.9; magnesium chloride hexahydrate 1.1; dextrose 5.9; disodium salt of ethylenediaminetetraacetic acid 0.027 and ascorbic acid 0.057), oxygenated with a mixture of 95% oxygen and 5% carbon dioxide and maintained at a temperature of 37° C. They were then subjected, for 4 h, to a traction of 4 g, reduced to 2 g just before the beginning of the experiment. The tissue was then contracted with the study compound and the resulting tension was recorded using a Grass polygraph, model 7D and a force transducer. Two concentration/effect curves were plotted, with cumulative concentrations of compound (from 100 nmol/1 to 3 mmol/l), and then an $\alpha_1$-antagonist, alfuzosin, was added to the bath at a concentration of 1 μmol/l, left in contact with the tissue for 30 min. Another concentration/effect curve was then plotted and compared with the second control curve.

The $\alpha_1$-agonist effect is measured by the concentration causing a contraction equal to 50% of the maximum effect.

For the compounds of the invention, this concentration varies between 1.3 and 2.6 μmol/l.

These results show that the compounds of the invention have in vitro agonist properties with respect to $\alpha_1$-type adrenergic receptors. The compounds of the invention can thus be used in the treatment of urinary incontinence.

The compounds of the invention can be produced in any suitable form, in combination with any suitable excipient, for oral or parenteral administration; for example in the form of tablets, dragees, capsules, solutions, and the like.

The daily dosage can vary from 0.1 to 20 mg/kg orally.

We claim:

1. Pyrrole derivative of the formula:

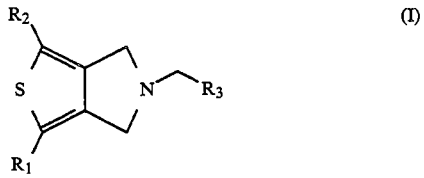

in which $R_1$ represents a hydrogen or halogen atom, a linear or branched $C_{1-6}$ alkyl group, a $C_{3-6}$ alkenyl group, a ($C_{1-4}$ alkoxy)methyl group, benzyl, a phenyl group unsubstituted or substituted by one or more halogen atoms or alkyl radicals, a $CO_2R$ group in which R represents a linear or branched $C_{1-4}$ alkyl radical, phenyl or benzyl, or a $CONR'R''$ group in which R' and R'' each represent, independently of one another, a hydrogen atom or a linear or branched $C_{1-4}$ alkyl radical, $R_2$ represents a hydrogen or halogen atom or a linear or branched $C_{1-4}$ alkyl group, and $R_3$ represents a 4,5-dihydro-1H-imidazol-2-yl or 1H-imidazol-4-yl group or its addition salt with pharmaceutically acceptable acids.

2. Pyrrole derivative according to claim 1, in which $R_3$ represents 4,5-dihydro-1H-imidazol-2-yl.

3. Pyrrole derivative according to claim 1, in which $R_3$ represents 1H-imidazol-4-yl.

4. 1-Ethyl-5-[(4,5-dihydro-1H-imidazol-2yl)methyl]-5,6-dihydro-4H-thieno[3,4-c]pyrrole dihydrochloride.

5. 1-Ethoxycarbonyl-5-[(4,5-dihydro-1H-imidazol-2-yl)methyl]-5,6-dihydro-4H-thieno- [3,4 -c]pyrrole dihydrochloride.

6. 1,3-Dibromo-5- [(4,5-dihydro-1H-imidazol-2-yl)methyl]-5,6-dihydro-4H-thieno[3,4-c ]pyrrole.

7. 1-Chloro-5-[(4,5-dihydro-1H-imidazol-2-yl)methyl]-5,6-dihydro-4H-thieno[3,4-c]pyrrole dihydrochloride.

8. A pharmaceutical composition useful as an $\alpha_2$-antagonist or $\alpha_1$-agonist comprising a compound of formula (I) as claimed in claim 1 in combination with a suitable excipient.

* * * * *